(12) United States Patent
Ryu et al.

(10) Patent No.: US 6,392,078 B1
(45) Date of Patent: May 21, 2002

(54) PROCESS AND CATALYST FOR MAKING DIALKYL CARBONATES

(75) Inventors: J. Yong Ryu, League City, TX (US); Abraham P. Gelbein, Falls Church, VA (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 09/866,340

(22) Filed: May 25, 2001

Related U.S. Application Data

(60) Provisional application No. 60/212,061, filed on Jun. 12, 2000.

(51) Int. Cl.[7] .............................................. C07C 69/96
(52) U.S. Cl. ..................................................... 558/277
(58) Field of Search ......................... 558/277; 502/156; 203/60

(56) References Cited

U.S. PATENT DOCUMENTS

| 4,137,242 A | 1/1979 | Prescher et al. ....... 260/348.25 |
| RE30,945 E | 5/1982 | Prescher et al. ............ 549/526 |
| RE31,381 E | 9/1983 | Prescher et al. ............ 549/526 |
| 5,214,185 A | 5/1993 | Nishihira et al. ........... 558/277 |
| 5,902,894 A * | 5/1999 | Ryu ........................... 558/277 |
| 6,010,976 A | 1/2000 | Ryu ........................... 502/156 |

FOREIGN PATENT DOCUMENTS

EP 0 742 198 A1 11/1996

* cited by examiner

Primary Examiner—Joseph K. McKane
Assistant Examiner—Joseph Murray
(74) Attorney, Agent, or Firm—Kenneth H. Johnson

(57) ABSTRACT

A process for producing dialkyl carbonates, such as dimethyl carbonate, from the reaction of a primary alcohol with urea in the presence of a catalyst which is a complex compound represented by $R_2Sn(OCH_3)_{2-\chi}L$, wherein $R=C_nH_{2n+1}$, n=1 to 12, $\chi$=1 or 2, and L is oxygen atom containing organic complexing agent which is carried out by conducting the reaction continuously under reactive distillation conditions wherein the product DMC is stripped from the reaction mixture with methanol and further including the recovery of product dimethyl carbonate (DMC) made in the process by contacting a stream containing the DMC, such as a azeotropic mixture with methanol, with diethyl oxylate under conditions of extractive distillation to selectively separate the DMC from methanol.

13 Claims, 7 Drawing Sheets

2 cc/min Ovhd Rate

Extractive Distillation of MeOH - DMC
Diethyl Oxalate Solvent

20: Mixer for preparation of urea solution     10: Reactive distillation column reactor

PROCESS AND CATALYST FOR MAKING DIALKYL CARBONATES

This application claims benefit of U.S. Provisional No. 60/212,061 filed Jun. 12, 2000.

BACKGROUND OF THE INVENTION

1. Field of the Invention

The present invention relates to a process for the production of dialkyl carbonates, particularly dimethyl carbonate wherein the reaction occurs simultaneously with separation of the reactants and the carbonate products. More particularly the invention relates to a process wherein methanol is reacted with urea and/or alkyl carbamate in the presence of a complex compound catalyst comprising an organic tin compound and an electron donor oxygen atom containing compound.

2. Related Art

Dialkyl carbonates are important commercial compounds, the most important of which is dimethyl carbonate (DMC). Dimethyl carbonate is used as a methylating and carbonylating agent. It can also be used as a solvent to replace halogenated solvents such as chlorobenzene. Although the current price of dimethyl carbonate is prohibitively expensive to use as fuel additive, it could be used as an oxygenate in reformulated gasoline and an octane component. Dimethyl carbonate has a much higher oxygen content (53%) than MTBE (methyl tertiary butyl ether) or TAME (tertiary amyl methyl ether), and hence not nearly as much is needed to have the same effect. It has a RON of 130 and is less volatile than either MTBE or TAME. It has a pleasant odor and, unlike ethers, is more readily biodegradable.

In older commercial processes dimethyl carbonate was produced from methanol and phosgene. Because of the extreme toxicity and cost of phosgene, there have been efforts to develop better, non-phosgene based processes.

In one new commercial process, dimethyl carbonate is produced from methanol, carbon monoxide, molecular oxygen and cuprous chloride via oxidative carbonylation in a two step slurry process. Such a process is disclosed in EP 0 460 735 A2. The major shortcomings of the process are the low production rate, high cost for the separation of products and reactants, formation of by-products, high recycle requirements and the need for corrosion resistant reactors and process lines.

Another new process is disclosed in EP 0 742 198 A2 and EP 0 505 374 B1 wherein dimethyl carbonate is produced through formation of methyl nitrite instead of the cupric methoxychloride noted above. The by-products are nitrogen oxides, carbon dioxide, methylformate, etc. Dimethyl carbonate in the product stream from the reactor is separated by solvent extractive distillation using dimethyl oxalate as the solvent to break the azeotropic mixture. Although the chemistry looks simple and the production rate is improved, the process is actually very complicated because of the separation of a number of the materials, balancing materials in various flow sections of the process, complicated process control and dealing with methyl nitrite, a hazardous chemical.

In another commercial process dimethyl carbonate is produced from methanol and carbon dioxide in a two step process. In the fist step cyclic carbonates are produced by reacting epoxides with carbon dioxide as disclosed in U.S. Pat. Nos. 4,786,741; 4,851,555 and 4,400,559. In the second step dimethyl carbonate is produced along with glycol by exchange reaction of cyclic carbonates with methanol. See for example Y. Okada, et al "Dimethyl Carbonate Production for Fuel Additives", ACS, Div. Fuel Chem., Preprint, 41(3), 868, 1996, and John F. Knifton, et al, "Ethylene Glycol-Dimethyl Carbonate Cogeneration", Journal of Molecular Chemistry, vol. 67, pp 389–399, 1991. While the process has its advantages, the reaction rate of epoxides with carbon dioxide is slow and requires high pressure. In addition the exchange reaction of the cyclic carbonate with methanol is limited by equilibrium and methanol and dimethyl carbonate form an azeotrope making separation difficult.

It has been known that dialkyl carbonates can be prepared by reacting primary aliphatic alcohols such as methanol with urea in the presence of various heterogeneous and homogeneous catalysts such as dibutyltin dimethoxide, tetraphenyltin, etc. See for example P. Ball et al, "Synthesis of Carbonates and Polycarbonates by Reaction of Urea with Hydroxy Compounds",C1 Mol. Chem. vol. 1, pp 95–108, 1984. Ammonia is a coproduct and it may be recycled to urea as in the following reaction sequence.

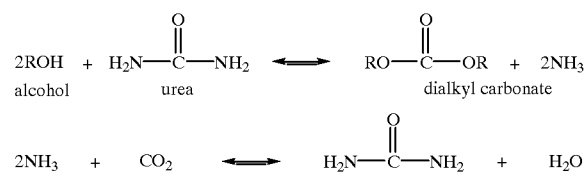

Carbamates are produced at a lower temperature followed by production of dialkyl carbonates at higher temperature with ammonia being produced in both steps.

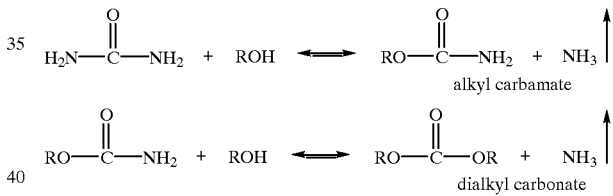

As noted the above two reactions are reversible under reaction conditions. The order of catalytic activity of organotin compounds is $R_4Sn<R_3SnX<<R_2SnX_2$, wherein X=Cl, RO, RCOO, RCOS. A maximum reaction rate and minimum formation of by-products are reported for dialkyl tin (IV) compounds. For most catalysts (Lewis acids), higher catalyst activity is claimed if the reaction is carried out in the presence of an appropriate cocatalyst (Lewis base). For example, the preferred cocatalyst for organic tin (IV) catalysts such as dibutyltin dimethoxide, dibutyltin oxide, etc. are triphenylphosphine and 4-dimethylaminopyridine. However, the thermal decomposition of intermediate carbamates to isocyanic acid (HNCO) or isocyanuric acid ((HNCO)$_3$) and alcohols is also facilitated by the organotin compounds such as dibutyltin dimethoxide or dibutyltin oxide employed in the synthesis of aliphatic carbamates. WO 95/17369 discloses a process for producing dialkyl carbonate such as dimethyl carbonate in two steps from alcohols and urea, utilizing the chemistry and catalysts published by P. Ball et al. In the first step, alcohol is reacted with urea to produce an alkyl carbamate. In the second step, dialkyl carbonate is produced by reacting further the alkyl carbamate with alcohol at temperatures higher than the first step. The reactions are carried out by employing an autoclave reactor. However, when methanol is reacted with methyl carbamate or urea, N-alkyl by-products such as N-methyl methyl carbamate (N-MMC) and N-alkyl urea are also produced. The dialkyl carbonate is present in the reactor in an amount between 1 and 3 weight % based on total carbamate and alcohol content of the reactor solution to minimize the formation of the by-products.

In U.S. Pat. No. 5,902,894, dimethyl carbonate (DMC) is synthesized from urea and methanol in high yield in a single step in the presence of high boiling ethers and a novel homogeneous tin complex catalyst.

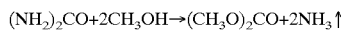

$(NH_2)_2CO + 2CH_3OH \rightarrow (CH_3O)_2CO + 2NH_3\uparrow$

The ether solvent also serves as complexing agent to form the homogenous complex catalyst from dibutyltin dimethoxide or oxide in situ.

The separation of materials involved in the DMC processes is very important for the commercial production of DMC for economic reasons. EP 0 742 198 A1 and U.S. Pat. No. 5,214,185 disclose the separation of DMC from a vapor mixture of methanol and DMC by using dimethyl oxalate (DMOX) as extraction solvent. Because of the high melting point of DMOX (54° C.), using DMOX is inconvenient and adds an extra cost to the separation. In the present invention a new material has been found to provide for a superior separation. Further, a novel method is disclosed for conducting the reaction continuously and with the simultaneous separation of the DMC product from the reaction mixture.

SUMMARY OF THE INVENTION

Dialkyl carbonates are prepared by reacting alcohols with urea or alkyl carbamate or both in the presence of a dibutyltin dimethoxide complex compound and high boiling oxygen containing organic solvent wherein the reaction is preferably carried out in the reboiler of a distillation still with concurrent distillation of the dialkyl carbonate. The complexing agent and the solvent are preferably the same compound. But they can be different oxygen containing organic compounds, if chosen to obtain the best performing environment to produce dialkyl carbonates such as dimethyl carbonate or diethyl carbonate. The concentration of homogeneous catalyst in the reaction zone is from 2 to 50%, preferably 3 to 40%. The concentration of electron donor oxygen containing solvent in the reaction zone is from 0.01% to 80%, preferably 3 to 65%.

In a preferred embodiment the complexing agents have one, two, three, four or more oxygen atoms per molecule, preferably two or more oxygen atoms per molecule preferably polyglycol ethers such as triglyme (triethylene glycol dimethyl ether), whose boiling point is higher than either methanol or dimethyl carbonate and which serve as both cocatalysts and solvent. In another preferred embodiment reaction is conducted continuously in a multistage distillation column where urea dissolved in methanol is introduced some number of stages above the reboiler, methanol vapor is introduced into the reboiler, and complex compound catalyst solution collected in the reboiler is circulated from the reboiler to some stage below from the methanol-urea feed stage via a pump. The downflowing reaction mixture is thus counter currently contacted with upflowing methanol vapor which strips the product DMC and ammonia from the reaction mixture. The column is configured with a reflux condenser and a number of stages above the methanol-urea feed stage. The column is operated with sufficient reflux vapors back down the column thus maintaining the catalyst solution inventory in the column.

Diethyl oxalate (DEOX) is preferably used as an extractive distillation solvent to separate DMC from the low-pressure azeotrope of DMC and methanol. DEOX has low melting point (–40° C.). Also it has higher boiling point (185.7° C.) than DMOX (164.5° C). In this utilization DEOX has more desirable properties than DMOX.

Also in the present process a small amount of amine, e.g., methylamine (MA) (b.p. 48° C.) may be produced. The MA and ammonia in the overhead stream from the catalytic distillation column is separated from the rest of the components in the stream by using a separator as overhead stream. Ammonia in the overhead stream from the separator is recovered as overhead product from the ammonia recovery column. MA is removed from the ammonia recovery column as bottom stream (organic waste). The bottom stream from the separator is composed of methanol and DMC, from which product DMC is separated as final pure product as shown later in FIG. 7.

Thus, the present invention provides an improved process by concurrently distilling dialkyl carbonate away from the reaction concurrently with the reaction and by preferably using specific complexing agents for the organotin complex catalyst. Since water is not coproduced, the reaction mixture (the overhead product) does not form a ternary azeotrope and, hence the separation of the product dimethyl carbonate from the overhead mixture is easier than the current commercial processes which have to deal with such a ternary azeotrope or prevent forming a ternary azeotrope.

DETAILED DESCRIPTION OF THE PREFERRED EMBODIMENT

Figure 1:
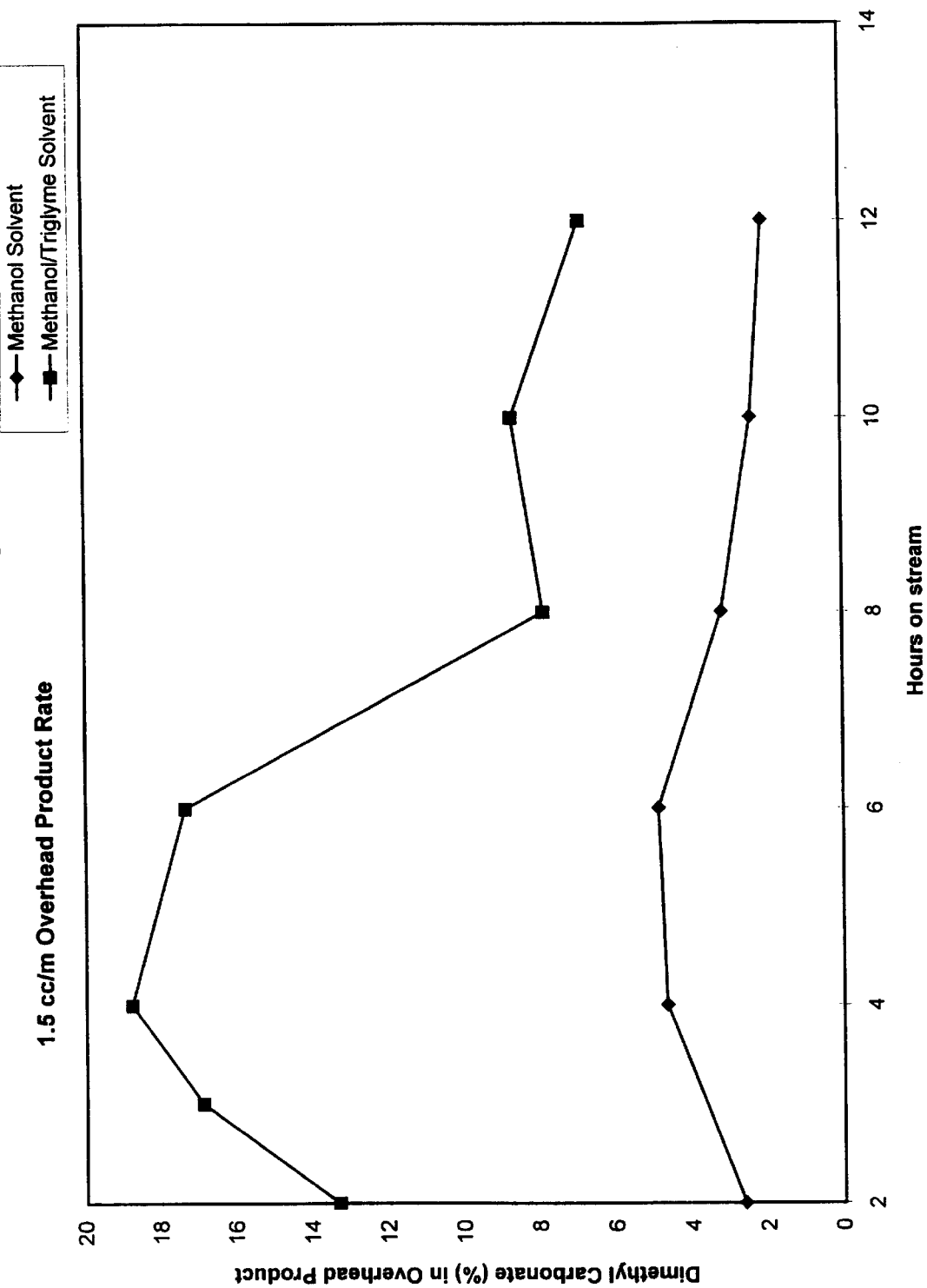
FIG. 1 is a plot of dimethyl carbonate in overhead product versus hours on stream comparing methanol only with methanol+triglyme.

The novel homogeneous organic tin complex catalysts of the present invention may be represented as:

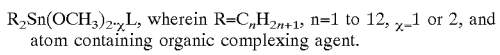

$R_2Sn(OCH_3)_{2-\chi}L$, wherein $R=C_nH_{2n+1}$, n=1 to 12, $\chi$=1 or 2, and atom containing organic complexing agent.

Both the high boiling oxygen containing solvent molecule and the complexing agent L for the homogeneous catalyst have at least one oxygen atom, preferably two or more oxygen atoms per molecule. The preferred solvent would have its boiling point higher than 60° C., preferably 90° C. and most preferably 110° C. under normal ambient atmospheric pressure. A mixture of two or more different such solvents or a mixture composed of such a solvent and a hydrocarbon solvent such as paraffinic, olefinic or aromatic compounds may be used. The preferred hydrocarbon solvent would have boiling point higher than 35° C. Both the preferred complexing agent L and the oxygen containing organic solvent have the oxygen containing functional groups such as ether group, carbonyl group, ester group, alcohol group or two different functional groups in a molecule. The examples of such compounds are diethylene glycol dimethyl ether, triethylene glycol dimethyl ether, tetraethylene glycol dimethyl ether, 1,3-dimethoxy propane, 1,2-dimethoxypropane, n-butyl ether, 1,4-dioxane, 2,3-pentanedione, 2,4-pentainedione, 1,3-dimethoxybenzene, 1,4-dimethoxybenzene, 3-methyl tetrahydrofuran, 2,5-dimethoxytetrahydrofuran, 6,7-dimethoxy-1-tetralone, 2,3-dimethoxytoluene, 2,3-dimethoxytoluene, 2,6-dimethoxytoluene, 3,3'-dimethoxybiphenyl, 4,4'-dimethoxybiphenyl, 2-methoxyethyl acetate, 2-methoxyethyl acetoacetate, 2-methoxyfuran, 2-[2-(2-methoxyethoxy)ethoxy]-1,3-dioxolane, 1-methoxy-2-propanol, 1,2-dimethoxypropane, 2-methoxytetrahydropyran, 5-methoxy-1-tetralone, 7-methoxy-2-tetralone, and the like. Various mixtures of two or more different compounds also can be used as both for solvent reaction medium and complexing agent for the organotin complex catalyst.

The reaction is preferably carried out in the presence of a high boiling electron donor oxygen containing solvent/complexing agent with the organotin compound, by employing the reboiler of distillation still or a distillation column as the reactor. The reactor temperature is controlled by changing the overhead pressure of the distillation column. The use of the reboiler and distillation column allows effective removal of the reaction products, dimethyl carbonate and ammonia, while keeping the homogeneous catalyst and solvent in the reactor. The column may be of any conventional form such as trays, packing, or combinations thereof.

The organotin complex catalyst may be prepared by mixing organotin compound with high boiling, oxygen containing compounds in situ in the reaction zone, e.g., the reboiler or distillation column at the initiation of the dialkyl carbonate reaction.

The reaction order of 2-methylhexyl carbamate in the presence of excess 2-ethylhexyl alcohol has been proposed to be pseudo first order, or less than one. Therefore, a lower methanol concentration relative to a given concentration of methyl carbamate is expected to be favorable for higher conversion rate of methyl carbamate. The use of both the reboiler-distillation column, and the high boiling oxygen atom(s) containing solvent such as diglyme (diethylene glycol dimethyl ether), triglyme (triethylene glycol dimethyl ether) or tetraglyme (tetraethylene glycol dimethyl ether), etc, allows carrying out the reaction under any desired pressure while maintaining any desired concentration of reactants (methanol, urea and carbamate) and product (dimethyl carbonate) in the reaction zone to obtain the best economical result.

In the present invention the desired ratio of the solvent to methanol in the reaction medium is controlled by changing the ratio of methanol to high boiling electron solvent at a given concentration of carbamate or a given combined concentration of urea and carbamate in the reboiler or the reaction zone. The use of the high boiling electron donor solvent as a complexing agent for the homogenous catalyst as well as a part of the reaction medium overcomes the shortcomings of the earlier processes.

Dimethyl carbonate is a highly active compound so in order to improve the selectivity to dimethyl carbonate, the concentration of dimethyl carbonate in the reboiler or the reaction zone should be kept as low as possible. In the present invention a very low concentration of dimethyl carbonate is obtained by selecting the proper high boiling solvent and controlling the overhead pressure which is a function of the ratio of methanol to high boiling electron donor solvent in the reboiler at a given concentration of methyl carbamate or given combination of methyl carbamate and urea. The use of the high boiling oxygen containing compounds as both cocatalyst and solvent improves the rate of forming dialkyl carbonates (because of effective removal of both ammonia and dimethyl carbonate from the reaction zone) and, at the same time, prevents the formation of by-products such as N-alkyl alkyl carbamate, alkyl amine, and N-alkyl urea or decomposition of urea or carbamate at relatively high concentration of dialkyl carbonate in both reactor and overhead products. High concentration of dialkyl carbonate in the overhead product reduces the cost of separating the dialkyl carbonate from methanol for recycle.

Since the reaction can be carried out at lower pressures (less than 120 psig) the present process has a number of advantages; lower cost for the material of construction, low catalyst inventory cost, easier removal of the ammonia and dimethyl carbonate products, and ease of control of the optimum concentration of methanol in the reactor for the maximum dimethyl carbonate formation rate and selectively to dimethyl carbonate.

Flushing out the reactor with an inert gas such as nitrogen or a light hydrocarbon although not necessary, be included as part of the startup. If inert gas is used to flush the reboiler the lower pressures preferably used in the present reaction system allows for the use of a blower instead of a compressor for the inert gas.

The preferred range of reactor temperature is from 270 to 400° F., preferably from 300–380° F. The preferred overhead pressure is within the range of 10–250 psig, more preferable between 20–200 psig and most preferably between 25–150 psig. The desirable weight ratio of high boiling electron donor solvent to methanol in the reactor is from 100–0.01:1, preferably 50–0.1:1. The preferred concentration of organotin compounds in the reactor is from 0.5 to 50 wt. %, preferably from 2–40 wt. % based on the total content in the reactor. The preferred overhead product rate is controlled to have from 4–35 per cent by weight dimethyl carbonate, preferably form 5–25 wt. %. The preferred concentration of methyl carbamate or combined concentration of methyl carbamate and urea in the reactor is from 5–60 wt. %, preferably from 15–55 wt. % during continuous operation.

For the continuous production of dimethyl carbonate, the urea solution may be directly pumped into the reactor or partially or completely converted to methyl carbamate prior to pumping into the reactor. Such conversion could be accomplished in a feed preheater or in separate reactor. The solvent for the urea solution can be substantially pure methanol or very dilute dimethyl carbonate solution in methanol. An example of the dilute dimethyl carbonate solution (about 2% dimethyl carbonate in methanol) is the overhead recycle stream from a dimethyl carbonate recovery column. In one embodiment all or a portion of the urea solution may be fed to the distillation column instead of the reboiler to partially convert urea to methyl carbamate prior to entering the reboiler. In another embodiment material from the reboiler may be added to the distillation column with the urea feed stream or at some other point below the feed point of the column.

Figure 6:
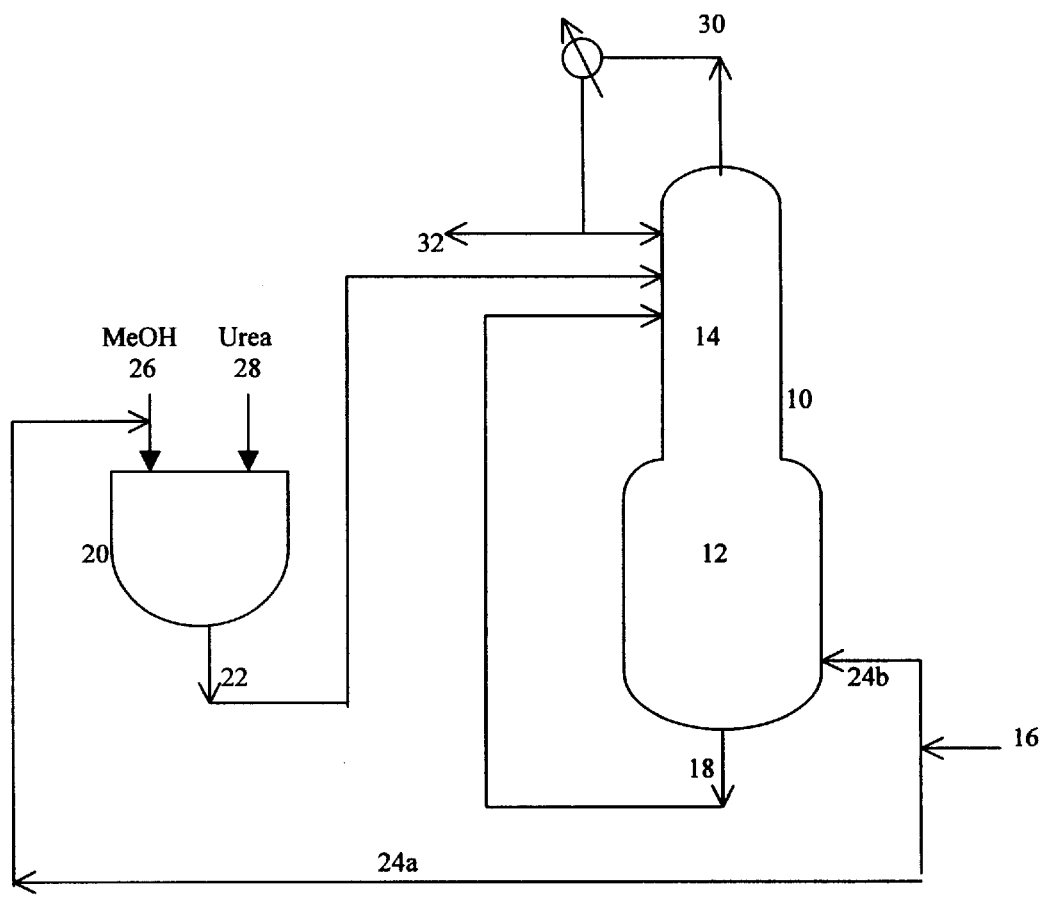
FIG. 6 is a schematic representation of a reactive distillation system for carrying out the present reaction.

Referring now to FIG. 6 the reactive distillation column reactor 10 is configured with a lower multiple staged reaction zone 12 (includes the reboiler since the catalyst is dissolved) and upper multiple staged distillation zone 14 as shown in the FIG. 6. The methanol/urea (2.57/1 mole ratio) feed solution is prepared in mixer 20 by dissolving granular solid urea in a mixture of fresh methanol feed and a part of recycle stream 16, and introduced via 22 to the top of the reaction zone together with a circulating stream 18 from the reboiler. Optionally the methanol/urea feed solution can be prepared in an inline mixer by mixing molten liquid urea stream with a mixture of fresh methanol stream 26 and a part of recycle stream 16. The recycle stream 16 is split with a portion 24 going to reboiler 12 and a portion going to the mixer 20. Urea is added via line 28 to the mixer. The urea feed solution stream 22 is preheated to about 150° F. and introduced to the top section of the reactive distillation column reactor 10. The circulating bottom stream 18 is composed of the high boiling solvent, catalyst, urea, methyl carbamate, NMMC (N-methyl methyl carbamate), etc. Urea reacts with methanol to produce methyl carbamate and ammonia, while it is flowing down the distillation column. Mainly methyl carbamate (MC) and ammonia are produced in the upper section of the reactive distillation column reactor, DMC and ammonia are produced in middle and lower section of the distillation column reactor. DMC and ammonia in the high boiling solvent are boiled off from the reaction medium and stripped off by methanol vapor introduced to the reboiler 12 as the stream 24b. Relatively larger pressure drop will be developed across the column length than in a normal distillation column operation which can be achieved with a high liquid level tray design or by operating a packed column in the so-called "froth" mode. The flow rate of this stream and the overhead pressure of the reactive distillation column were adjusted to obtain a reboiler temperature sufficiently high enough to convert urea/MC to dimethyl carbonate at a desired rate. The range of temperature to convert urea/MC to dimethyl carbonate is from 220 to 550° F., preferably from 240 to 500° F., most preferably from 250 to 400° F. The range of overhead pressure will be depend on the boiling point of high boiling oxygen containing solvent, the composition of the liquid flowing down inside of the distillation column and finally the rate of the circulating bottom stream 18. The preferred range of overhead pressure is from 25 to 250 psig, preferably 30 to 220 psig, most preferably from 40 to 200 psig. When triglyme is the oxygen containing solvent, the overhead pressure is about 110 psig.

Figure 7:
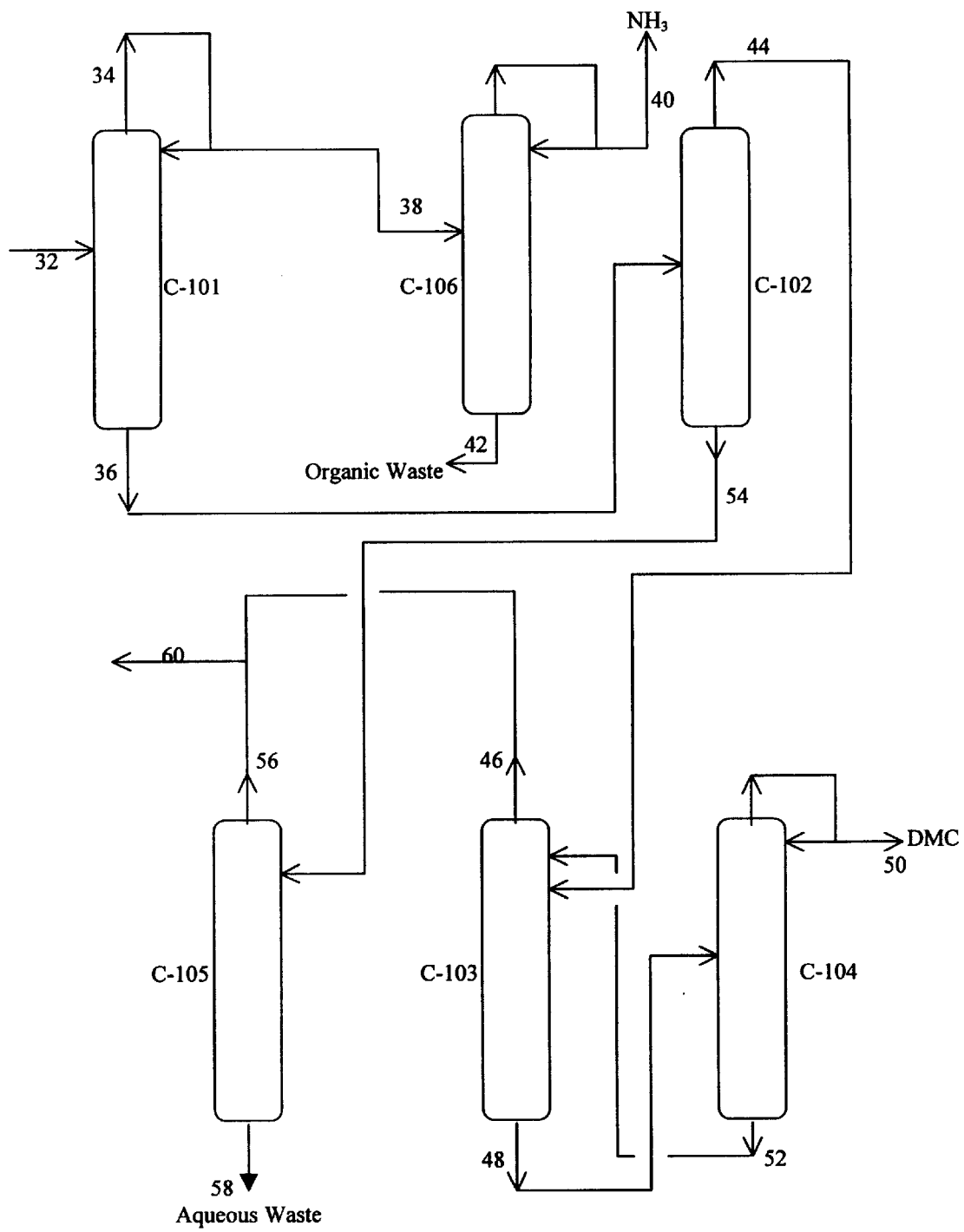
FIG. 7 is schematic representation of a product recovery section or DMC.

The separation of the reaction products is illustrated in FIG. 7. The hot vapor stream 30 from the top of the reactive distillation column reactor 10 contains DMC, methanol, methylamine, and ammonia. It is condensed to reflux by cooling in a heat exchanger (as shown in FIG. 6) and then the stream 32 pumped into the ammonia stripper C101. The ammonia stripper is operated at 350° F. and 275 psig. The overhead stream 34 from the stripper is cooled by a heat exchanger (not shown) for reflux and then the condensed stream 38 is pumped into the ammonia recovery column C-106. The ammonia recovery column is operated at 200° F. and 275 psig. Ammonia is recovered as the overhead stream 40, and methylamine is recovered as a part of organic waste stream from the bottom stream 42.

The bottom liquid stream 36 from the ammonia stripper C101 is fed to the azeotrope column C-102 operated at 160° F. and 19 psig, which functions to separate DMC as a low boiling azeotrope (about 32 wt % DMC at 19 psi), with methanol as the overhead stream 44. The bottom product 54 composed of mostly methanol and a trace of water is sent to the methanol recovery column C-105. The methanol recovery column is operated at 170° F. and 19 psig. The recovered methanol as the overhead stream 56 is recycled.

DMC in the DMC-methanol azeotrope 44 from the azeotrope column C-102 is sent for DMC recovery in the extractive distillation column C-103 using DEOX (diethyl oxalate) as the solvent. The vapor azeotrope stream 44 is cooled to condense (not shown) and the condensed stream 44 is fed near the middle of the extractive column C-103 (operating at 350° F. and 17 psig) while the solvent stream 52 is fed near the top of the column. The mass ratio of solvent: feed for the column C-103 is approximately 9:1. The extract phase 48 contains the net make of DMC. The distillate phase 46, comprising methanol and a small amount of DMC (about 2.5 mole %) is combined with the overhead stream 56 from the methanol recovery column C-105 and the combined stream 60 is recycled to the reactive distillation column 10 and the mixer 20. (The combined stream 60 becomes stream 16 in FIG. 6). The DMC product (better than 99.99 wt % purity) is finally recovered from the extract phase in the DMC column C-104 operated at 400° F. and 19 psig as the distillate product stream 50. The solvent (containing less than 0.1 wt % DMC) is the bottom product 52 and is recycled to the extractive distillation column C-103.

EXAMPLE 1

Figure 2:
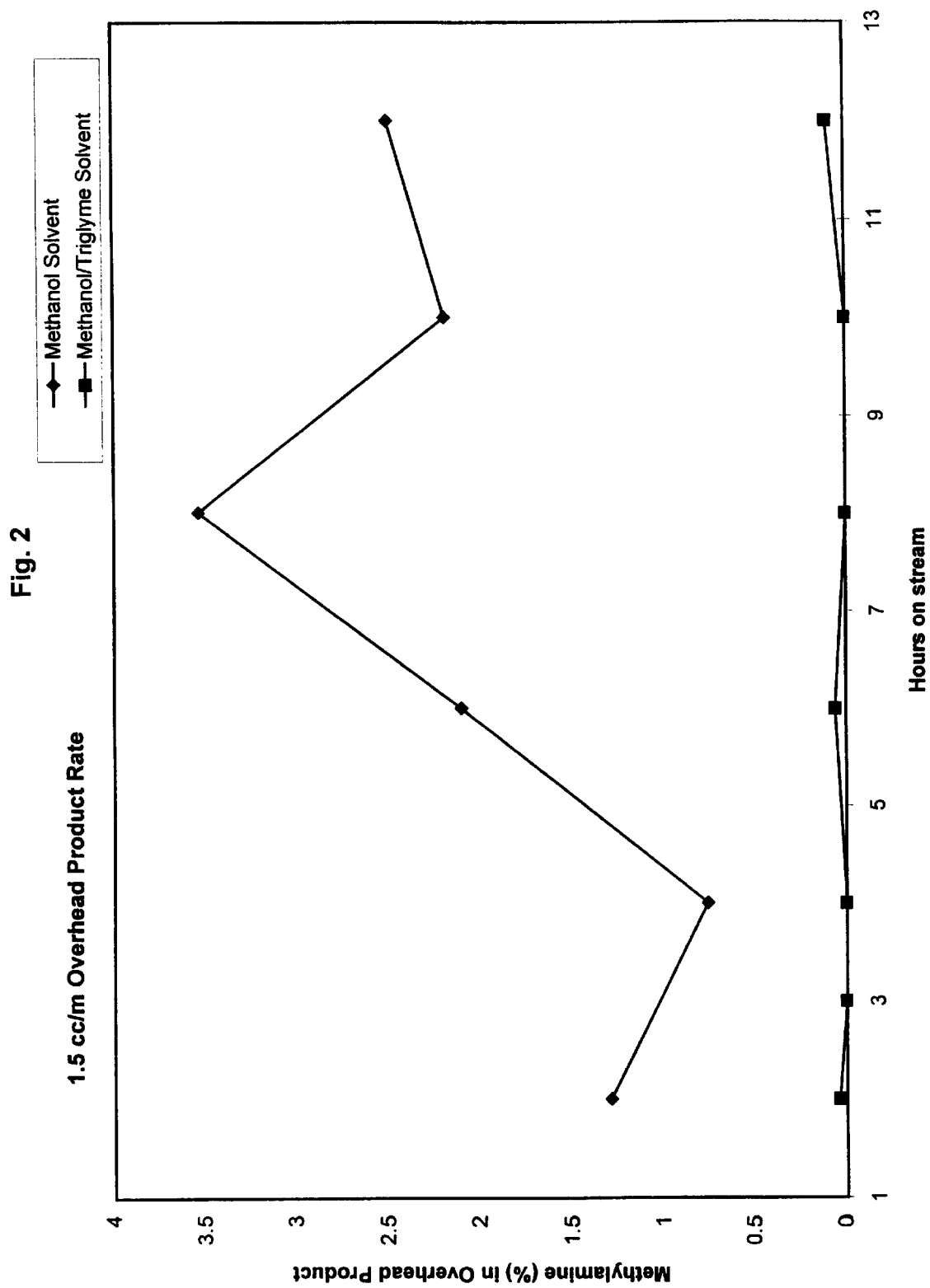
FIG. 2 is a plot of methylamine in overhead product versus hours on stream comparing methanol only with methanol+triglyme.

The reaction was carried out in the reboiler (350 ml) of a distillation still. The distillation column was ¼" diameter and 18" long, which was packed with ⅛" ceramic saddles. The reboiler was charged with 125 g MC (methyl carbamate), 200 g methanol and 25.3 g dibutyltin dimethoxide. The reboiler temperature was maintained at 355–363° F. by controlling the overhead pressure. The flow rate of the overhead product was set at 1.5 cc/min. Methanol was continuously pumped into the reboiler to maintain a constant liquid level in the reboiler. The reaction was carried out for 6 hours each day for 2 days, for a total of 12 hours. After a 6 hour run, the unit was shut down. On the following day the unit was restarted. During the reaction the overhead liquid products were collected into a reservoir. At the end of the run all the composite overhead liquid product in the reservoir and the inventory materials in the reboiler and column were removed from the system and weighted and then analyzed. During the run the samples taken from the unit for analysis were also weighted. The result is listed in Table 1. The change in the compositions of DMC and methylamine in the overhead liquid products during the run is illustrated in FIGS. 1 and 2, respectively. The overhead pressure at 355° F. at the beginning and the end were 268.4 and 374.4 psig, respectively. The column temperatures at the bottom and top section of the column were 332° F. and 321° F. at the beginning, and 353° F. and 348° F. at the end of 12 hours run. The analysis of the bottom product sample taken from the reboiler at the end of 12 hours indicated trace ammonia, 6.9% DMC, 3.6% N-MMC, 2.1% MC, 86.6% methanol, and 0.7% others. The overhead product contained 2.1% DMC and 2.5% methylamine. The content of urea in the bottom product sample was unknown because urea could not be analyzed by gas chromatography due to urea decomposition.

TABLE 1

| Example | 1 | 2 |
|---|---|---|
| Solvent | 200 MeOH | 100 MeOH/100 TRIGLYME |
| Reboiler Temp, ° F. | 355 | 355 |
| Ovhd P, psig | | |
| Initial | 268.4 | 53.4 |
| Final | 374.4 | 139 |

TABLE 1-continued

| Example | 1 | 2 |
|---|---|---|
| Rate, cc/min | 1.5 | 1.5 |
| Mass Balance, % | 105.7 | 103.1 |
| Mole Balance*, % | 41.0 | 94.0 |
| Apparent MC Conv, m % | 93.2 | 95.9 |
| Apparent Selectivity*, m % | | |
| DMC | 31.8 | 90.2 |
| N-MMC | 8.9 | 0.6 |
| DMC removed as ovhd product, g | 23.2 | 99.2 |

*The urea content in the reboiler was not included in the calculation.

EXAMPLE 2

The reboiler of the distillation still was charged with 125 g MC, 100 g methanol, 100 g triglyme and 24.7 g dibutyltin dimethoxide. The reboiler temperature was maintained at 355–363° F. by controlling the overhead pressure. The flowrate of the overhead liquid product was set at 1.5 cc/min. To maintain a constant liquid level in the reboiler, a mixture of methanol and triglyme was prepared by mixing 1650 g methanol with 142.5 g triglyme was continuously pumped into the reboiler. The reaction was carried out for 6 hours each day for 2 days, for a total of 12 hours. The result of this experiment is listed in Table 1. The change in the compositions of DMC and methylamine in the overhead liquid products during the run are illustrated in FIGS. 1 and 2, respectively. The overhead pressures at 355° F. at the beginning and the end were 53.4 psig and 139 psig, respectively. The column temperatures at the bottom and top section of the column were 234° F. and 200° F. at the beginning, and 288° F. and 277° F. at the end of 12 hours run. The analysis of the bottom product sample taken from the reboiler at the end of 12 hours run indicated 0.1% ammonia, 4.1% DMC, 0.3%N-MMC, 2.7% MC, 32.6% methanol, and 60.2% triglyme. The overhead product contained 6.9% dimethyl carbonate. The content of urea could not be analyzed by gas chromatography due to decomposition of urea.

Example 2 demonstrates the superior yield and selectivity for DMC of the present invention compared with the prior art (the Example 1). It also demonstrates that the reaction can be carried out under much lower pressure in the presence of the high boiling electron donating oxygen containing solvent, resulting in fast removal of the products DMC and ammonia from the reaction zone as soon as they are produced. Because of the fast removal of the products DMC and ammonia from the reaction zone and the novel organotin complex catalyst $Bu_2Sn(OCH_3)_{2-x}L_x$ ($x$=1 or 2), the superior selectivity to DMC is obtained. The DMC content in the overhead liquid product of the present invention was at least 3 times higher than the dibutyltin dimethoxide catalyst alone and in the absence of the solvent triglyme (Example 1). Consequently the separation of dimethyl carbonate from the overhead product can be achieved at much lower cost and much reduced amount of material recycle. The low reactor pressure and non-corrosive reaction system results in a great cost advantage from prior systems.

EXAMPLE 3

Figure 3:
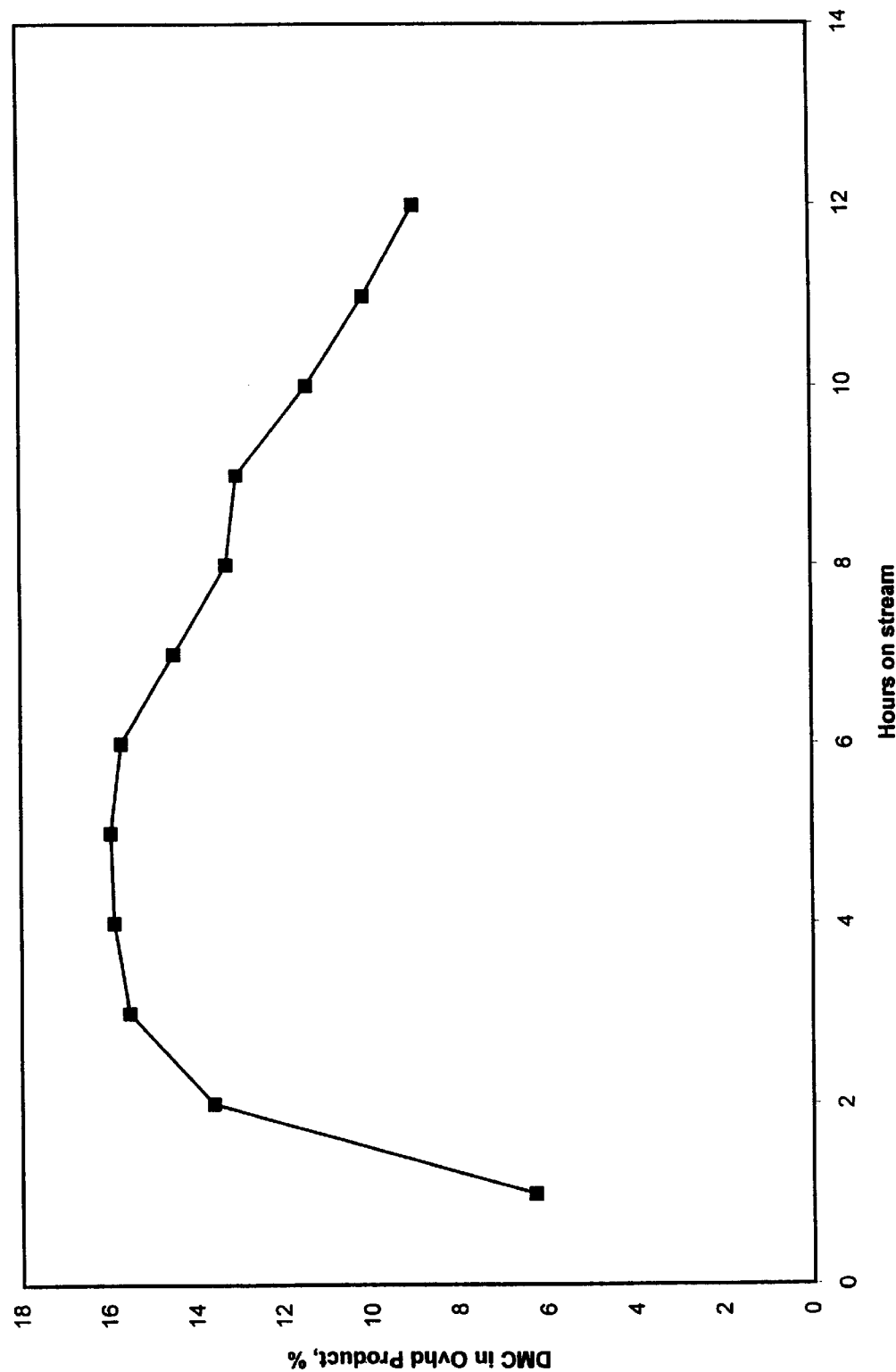
FIG. 3 is a plot of DMC in the overhead product taken hourly over the duration of the run Example 3.

This Example illustrates the actual production of DMC by one step. The reboiler of the distillation still was charged with 125 g methyl carbamate, 120 g methanol, 80 g triglyme and 25 dibutyltin dimethoxide. The reboiler temperature was maintained at 349–357° F. by controlling the overhead pressure during the 12 hours uninterrupted run. The flow rate of the overhead liquid product was set at 2 cc/min. A urea solution prepared by dissolving 105.6 g urea in 2200 g methanol was pumped into the reboiler to maintain a constant liquid level in the reboiler. The reaction was terminated after 12 hours uninterrupted operation. The result of this experiment is listed in Table 2. The change of the DMC composition in the overhead products is shown in FIG. 3. The overhead pressures at the beginning and the end of 12 hours run were 66 and 134.7 psig, respectively. The column temperatures at the bottom and top section of the column were 248° F. and 233° F. at the beginning, and 286° F. and 274° F. at the end of 12 hours, respectively. While the analysis of the sample taken from the reboiler a the end of 12 hours run indicated 3.8% dimethyl carbonate, 20.9% methanol, 21.1% methyl carbamate, 1.5% N-MMC, 52.0% triglyme, 0.2% unknown, 0.2% methylamine (or water) and 0.3% ammonia, the overhead product contained 9.0% dimethyl carbonate, 88.4% methanol, 0.1% methylamine (or water) and 2.5% ammonia. The content of urea in the bottom product sample was unknown because urea could not be analyzed by gc due to urea decomposition. The unit was shut down for the next day's run. The weight of the composite overhead product was 1054 g and the weight of the urea solution pumped into the reboiler was 1252 g. The total samples taken out from the unit was 210.8 g. There was lower liquid level in the reboiler from 8 to 12 hours on stream. The composite overhead product contained 11.5% dimethyl carbonate. A vent gas was collected for 12 hours during the reaction (very little gas volume) and the analysis of this vent gas indicated 0.05 vol % $CO_2$ and 2.1 vol $O_2$ indicating very little decomposition of methyl carbamate or urea.

Samples of the overhead product were taken hourly over the duration of the run. The DMC concentration in these samples is illustrated in FIG. 3. The result of this experiment is summarized in Table 2. The maximum concentration of DMC was ~16 wt % in the 5 hr sample. The productivity observed at 5 hr was assumed to be indicative of the space yield that could be achieved with the system under steady state conditions. The value was calculated to be ~3.4 lb DMC/hr-ft$^3$ (2 g/min×0.16/350 cm$^2$×60 min/hr×2.2E−0.3 lb/g×2.832E+04 cm$^3$/ft$^3$). This value was used in sizing the reaction zone of the reactive distillation column.

The run was continued the next day by pumping a mixed solution prepared by mixing 1650 g methanol with 142.5 g triglyme into the reboiler. The reboiler temperature was maintained at 348–359° F. by controlling the overhead pressure. The flow rate of the overhead liquid product was set a 2 cc/min. The reaction was terminated after 10 hours uninterrupted operation. The result of this experiment is listed in Table 2. The overhead pressures at the beginning and the end of 10 hours uninterrupted run were 232.1 and 201.7 psig, respectively. The column temperatures at the bottom and top section of the column were 248° F. and 233° F. at the beginning, and 322° F. and 313° F. at the end of 10 hours run, respectively. While the analysis of the sample taken from the reboiler at the end of 10 hours (total 22 hours from the very beginning) run indicated 1.7% dimethyl carbonate, 22.2% methanol, 1.5% methyl carbamate, 1.3% N-MMC, 71.9% triglyme, 1.3% unknowns and 0.1% air, the overhead product contained 3.8% dimethyl carbonate, 94.94% methanol and 1.2% ammonia. The content of urea in the bottom product sample was unknown, because urea could not be analyzed by gc due to urea decomposition. The weight of the composite overhead product was 956 g and the weight of the mixed solution pumped into the reboiler was 1088. The total weight of the samples taken out from the unit was 197.2 g. The total weight of the inventory material collected from the column and the reboiler was 249. The vent gas was collected during the run (very small gas volume) and it contained 10.0 vol% $CO_2$ and 0.7 vol $O_2$.

High DMC concentration in the overhead product is very desirable because the DMC separation is a costly process due to the formation of binary azeotrope with methanol. As shown in Table 2 the DMC selectivity is excellent (98.2%). When the urea solution is pumped directly into the reboiler in the one step synthesis process, very little methyl carbamate decomposes.

TABLE 2

| Solvent | 120 MeOH/80 TG | |
| --- | --- | --- |
| Pump-in Solution | Urea in MeOH (12 hrs) | MeOH/TG (10 hrs) |
| Reboiler Temp, ° F. | 349–357 | 358–359 |
| Ovhd P, psig | | |
| Initial | 66 | 232.1 |
| Final | 134.7 | 201.7 |
| Ovhd Product Rat, cc/m | 2 | 2 |
| Mass Balance, % | 100.1 | |
| Mole Balance*, % | 99.8 | |
| App. Conversion*, % | 98.3 | |
| Selectivity*, % | | |
| DMC | 98.2 | |
| N-MMC | 1.6 | |
| DMC Recovered as | 151.3[1] | 209.1[2] |
| Ovhd Product, g | | |

App.; apparent
*Calculated based on combined methyl carbamate and urea consumed during the reaction, assuming no uncovered urea left in the reactor at the end of run.
[1]For the first 12 hours run.
[2]For the total 22 hours run.

EXAMPLE 4

This Example was carried out to demonstrate DEOX as extractive distillation solvent for the separation of DMC from azeotropic mixture. In the first part of this Example the vapor pressure of DMC at pressures other than atmospheric was determined. This was done in a distillation column of 1" diameter and 25' long.

Figure 4:
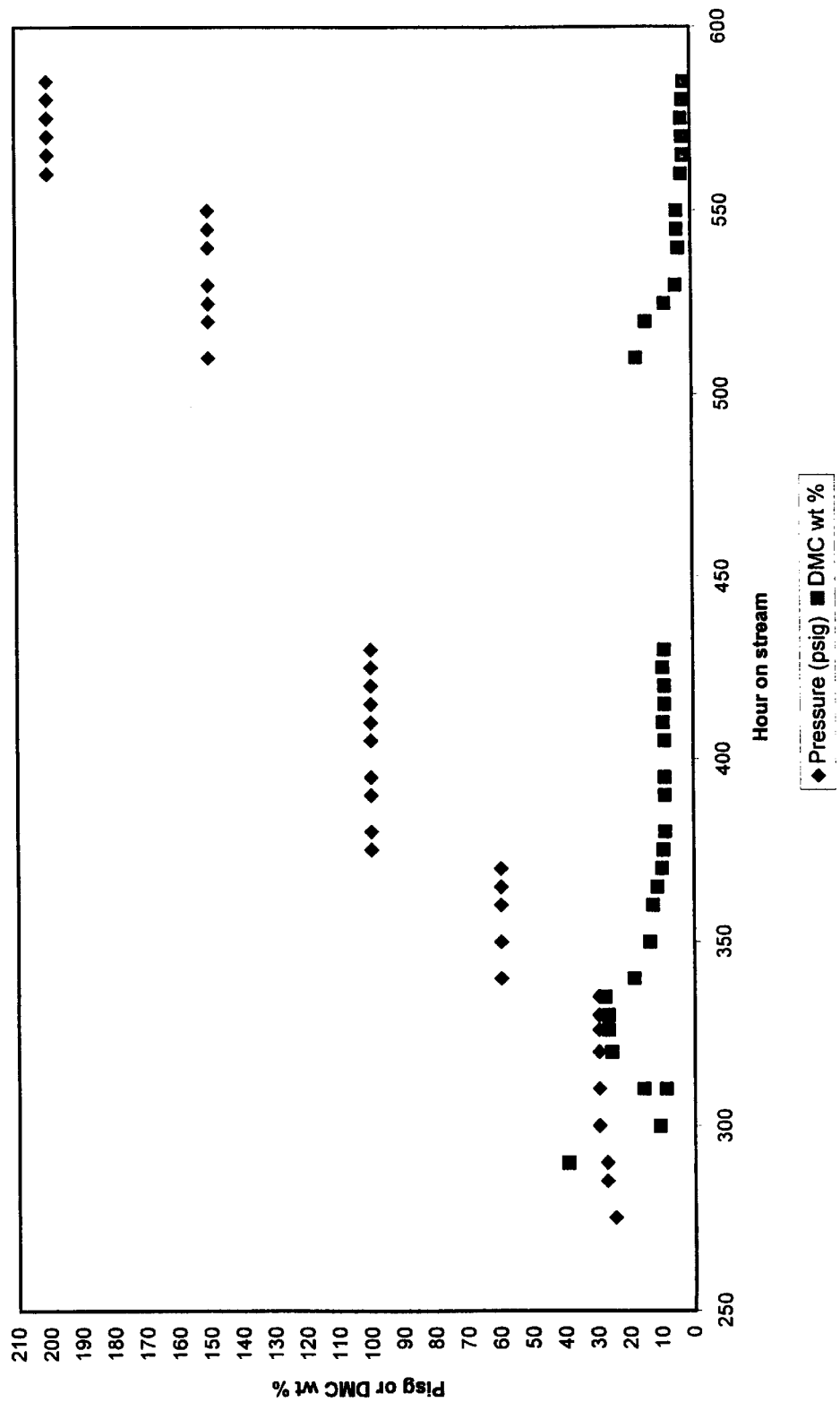
FIG. 4 is a plot showing the DMC/methanol azeotrope composition over a range of pressures.

The second part of this Example shows the vapor pressure and composition of the methanol-DMC azeotrope at higher pressures. This was done by feeding a mixture of methanol and DMC to the same distillation column used above. The azeotrope, known to be minimum-boiling, was the overhead stream while the balance of the feed went out the bottom. The data analysis of the result indicates that the actual azeotrope composition at atmospheric pressure is about 34 wt % rather than about 30 wt % as reported (Azeotropic data 111, compiled by Lee H. Horsley, The Dow Chemical Co.; ACS Advances in Chemistry Series, 1973). The results are illustrated in FIG. 4.

Figure 5:
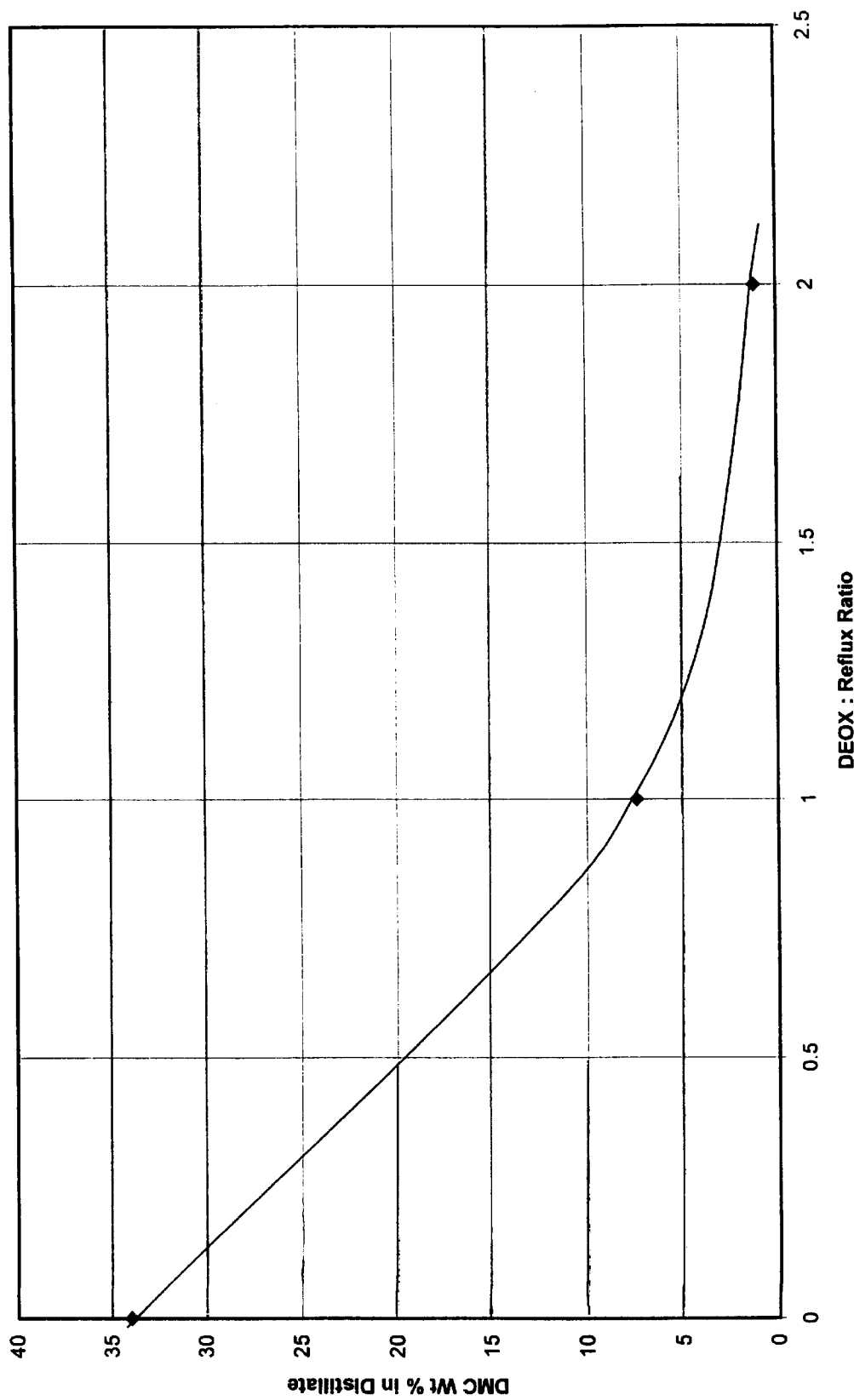
FIG. 5 is a plot showing the effectiveness of DEOX for extractive distillation of DMC rom DMC/methanol mixtures.

The third part of this Example was carried out in an 2" Oldershaw column. This was set up with 15 trays above a 2 liter pot, with a feed point at tray 10. After refluxing with a mixture of DMC and methanol richer in DMC than the azeotropic composition and sampling the distillate, DEOX was fed at a rate of about 40 ml/min and the distillate sampled twice. This was repeated, using a DEOX feed rate of 20 ml/min. The ratio of added DEOX to the liquid reflux (without DEOX addition) was about 2:1 for 40 ml/min addition, and about 1:1 for the 20 ml/min rate. The result is illustrated in FIG. 5. DEOX is an effective extractant, and a good separation of DMC from low pressure azeotropic mixture can be made by DEOX extractive distillation.

EXAMPLE 5

The following data illustrate the present process for a 2170 bbl DMC per day plant. Stream results are summarized in Tables 3 and 4.

TABLE 3

Capacity: 2170 bbl DMC/day
Material Streams

| STREAM | 26 | 28 | 22 | 32 | 18 | 32 | 38 | 40 | 42 |
| --- | --- | --- | --- | --- | --- | --- | --- | --- | --- |
| Vapor fraction | 0 | 0 | 0 | 0 | 0 | 0 | 0 | 0 | 0 |
| Tem, ° F. | 75 (100) | 75 | 150 | 191 | 352 | 191 | 117.1 | 116.9 | 195.7 |
| Press, psia | 50 | — | 110 | 100 | 110 | 275 | 275 | 273 | 274 |
| Mola flow, lb m/hr | 736.3 | 365 | 1575.3 | 6549 | 4598 | 6548.3 | 731.1 | 729 | 2.3 |
| STREAM | 36 | 44 | 46 | 48 | 50 | 52 | 54 | 56 | 60 |
| Vapor frac. | 0 | 0 | 0 | 0 | 0 | 0 | 0 | 0 | 0 |
| Temp, ° F. | 328.4 | 149.2 | 148.7 | 347.7 | 100 | 383 | 160.2 | 149.1 | 149.3 |
| Press, psia | 275 | 17 | 115 | 17 | 16 | 19 | 19 | 15 | 115 |
| Mola flow, lb m/hr | 5816.5 | 2707.5 | 2343.2 | 7064.4 | 364.3 | 6700.1 | 3109.1 | 3104.5 | 5447.7 |
| STREAM | 24a | 24b | | | | | | | |
| Vapor frac. | 0 | 1 | | | | | | | |
| Temp, ° F. | 149.3 | 375 | | | | | | | |
| Press, psia | 115 | 112 | | | | | | | |
| Mola flow, lb m/hr | 474 | 4973 | | | | | | | |

TABLE 4

Capacity: 2170 bbl DMC/day
Compositions
(Mole Fraction)

| Stream | 26 | 28 | 22 | 32 | 18 | 38 | 40 | 42 | 36 |
|---|---|---|---|---|---|---|---|---|---|
| Triglyme | 0 | 0 | 0 | 0 | 0.65 | 0 | 0 | 0 | 0 |
| Ammonia | 0 | 0 | 0 | 0.111 | 0 | 0.997 | 1 | 0.214 | 0. |
| MC | 0 | 0 | 0 | 0 | 0.048 | 0 | 0 | 0 | 0 |
| Methanol | 1 | 0 | 0.767 | 0.829 | 0.278 | 0.001 | 0 | 0.463 | 0.933 |
| DMC | 0 | 0 | 0.001 | 0.059 | 0.018 | 0 | 0 | 0.015 | 0.066 |
| H2O | 0 | 0 | 0 | 0 | 0 | 0 | 0 | 0 | 0 |
| CO2 | 0 | 0 | 0 | 0 | 0 | 0 | 0 | 0 | 0 |
| N-MMC | 0 | 0 | 0 | 0 | 0.006 | 0 | 0 | 0 | 0 |
| Urea | 0 | 1 | 0.232 | 0 | 0 | 0 | 0 | 0 | 0 |
| DEOX | 0 | 0 | 0 | 0 | 0 | 0 | 0 | 0 | 0 |
| MA | 0 | 0 | 0 | 0 | 0 | 0.001 | 0 | 0.308 | 0 |
| Stream | 44 | 46 | 48 | 50 | 52 | 54 | 56 | 60 | |
| Triglyme | 0 | 0 | 0 | 0 | 0 | 0 | 0 | 0 | |
| Ammonia | 0 | 0 | 0 | 0 | 0 | 0 | 0 | 0 | |
| MC | 0 | 0 | 0 | 0 | 0 | 0 | 0 | 0 | |
| Methanol | 0.857 | 0.991 | 0 | 0 | 0 | 1 | 1 | 0.996 | |
| DMC | 0.143 | 0.009 | 0.052 | 1 | 0 | 0 | 0 | 0.004 | |
| H2O | 0 | 0 | 0 | 0 | 0 | 0 | 0 | 0 | |
| CO2 | 0 | 0 | 0 | 0 | 0 | 0 | 0 | 0 | |
| N-MMC | 0 | 0 | 0 | 0 | 0 | 0 | 0 | 0 | |
| Urea | 0 | 0 | 0 | 0 | 0 | 0 | 0 | 0 | |
| DEOX | 0 | 0 | 0.948 | 0 | 1 | 0 | 0 | 0 | |
| MA | 0 | 0 | 0 | 0 | 0 | 0 | 0 | 0 | |

The invention claimed is:

1. A process for the production of dialkyl carbonates comprising the steps of:
    (a) feeding urea and a primary alcohol to a reaction zone;
    (b) feeding a complex compound represented by $R_2Sn(OCH_3)_2 \cdot \chi L$, wherein $R=C_nH_{2n+1}$, n=1 to 12, $\chi$=1 or 2, and L is oxygen atom containing organic complexing agent; and
    (c) concurrently in said reaction zone
        (i) reacting a portion of the primary alcohol and urea in the presence of said organotin compound and said high boiling electron donor atom containing solvent to produce dialkyl carbonate;
        (ii) removing the dialkyl carbonate and ammonia from said reaction zone as vapor and
        (iii) contacting said vapor from step (c)(ii) with DEOX under conditions of extractive distillation to selectively extract dialkyl carbonate.

2. The process according to claim 1 wherein ammonia and a portion of said alcohol are removed from said reaction zone as vapor and withdrawn along with said dialkyl carbonate as overheads.

3. The process according to claim 2 wherein said overheads are partially condensed to separate said ammonia as a vapor from said dialkyl carbonate and said alcohol as a liquid.

4. The process according to claim 1 wherein said $R_2Sn(OCH_3)_2$ is dibutyltin dimethoxide.

5. The process according to claim 1 wherein said $R_2Sn(OCH_3)_2$ compound comprises dibutyltin dimethoxide.

6. The process according to claim 1 wherein L comprises triethylene glycol dimethyl ether.

7. The process according to claim 1 wherein said $R_2Sn(OCH_3)_2$ comprises dibutyltin dimethoxide and L comprises triethylene glycol dimethyl ether.

8. The process according to claim 1 wherein said $R_2Sn(OCH_3)_2$ comprises dibutyltin dimethoxide and L comprises diethylene glycol dimethyl ether.

9. The process according to claim 1 wherein said primary alcohol comprises methanol and said dialkyl carbonate comprises dimethyl carbonate.

10. A process for recovering DMC from mixtures comprising contacting a DMC containing stream with DEOX under conditions of extractive distillation to selectively extract DMC into said DEOX.

11. The process according to claim 10 wherein said DMC containing stream contains methanol.

12. The process according to claim 10 wherein said DMC containing stream has previously been treated to remove $NH_3$ by fractionation.

13. The process according to claim 10 wherein said DMC containing stream is vapor phage.

* * * * *